United States Patent

Petty

Patent Number: 5,514,827
Date of Patent: May 7, 1996

[54] SILYLATED CYCLIC HYDROCARBONS AND THEIR USES

[75] Inventor: Herbert E. Petty, Bethel, Conn.

[73] Assignee: OSi Specialties, Inc., Danbury, Conn.

[21] Appl. No.: 378,160

[22] Filed: Jan. 25, 1995

[51] Int. Cl.$^6$ .................. C07F 7/08; C07F 7/10; C07F 7/18

[52] U.S. Cl. .......... 556/431; 556/435; 556/422; 556/482; 556/484; 556/486; 556/489; 556/465; 524/437; 524/547; 524/588; 528/15; 528/17

[58] Field of Search ..................... 556/422, 482, 556/484, 486, 489, 465, 471, 435; 524/437, 547, 588; 528/17, 15

[56] References Cited

U.S. PATENT DOCUMENTS

| | | |
|---|---|---|
| 3,334,067 | 8/1967 | Weyenberg . |
| 3,689,454 | 9/1972 | Smith et al. . |
| 3,772,065 | 11/1973 | Seiler . |
| 3,779,986 | 12/1973 | Smith et al. . |
| 3,941,733 | 3/1976 | Chang . |
| 4,100,129 | 7/1978 | Beers . |
| 4,342,796 | 8/1982 | Brown et al. . |
| 4,476,241 | 10/1984 | Dallavia, Jr. et al. . |
| 4,719,194 | 1/1988 | Cietek et al. . |
| 4,990,377 | 2/1991 | Wilson . |
| 5,032,636 | 7/1991 | Ono et al. . |
| 5,051,129 | 9/1991 | Cuthbert et al. . |
| 5,142,082 | 8/1992 | Sato et al. ............... 556/482 |
| 5,175,332 | 12/1992 | Chatterton et al. ........ 556/482 |
| 5,248,803 | 9/1993 | Aoki et al. ............... 556/482 |
| 5,264,606 | 11/1993 | Moloy et al. . |
| 5,359,114 | 10/1994 | Aoki et al. ............... 556/482 |

FOREIGN PATENT DOCUMENTS 9460807  3/1994  WIPO .

*Primary Examiner*—Paul F. Shaver
*Attorney, Agent, or Firm*—Andrew S. Reiskind

[57] ABSTRACT

This invention includes di- and tri(alkoxysilylalkyl)- or haloalkoxysilylalkylcyclic pentanes, which may have substituents thereon, including vinyl groups, and their use as waterproofing agents, as crosslinking agents in room temperature vulcanizing silicone caulks, in coating compositions and as surface treatments. The cyclic hydrocarbons are pentane ($C_5$). The silane groups are attached to the ring through an alkyl group, which may have substituents thereon. Multiple silane groups may be attached to the ring. The silanes may have the standard substituents thereon, including alkoxy and halogens.

The specific silanes contemplated herein have the following formula:

$$[R_a X_{3-a} Si(CR'_2)_n]_b cycloC_5 R''_{10-b}$$

where R is an alkyl or aryl group, X is a halogen or an alkoxy radical of 1 to 4 carbon atoms, aryloxy radical or oxime group, R' is a hydrogen or alkyl group of 1 to 3 carbon atoms, R" is a vinyl, alkyl, allyl, aryl, aryloxy or alkoxy group or hydrogen, a=0, 1 or 2, n=2 to 3 and if at least one R" is a vinyl or allyl group, b=1 to 5, otherwise b=2 to 5.

13 Claims, No Drawings

SILYLATED CYCLIC HYDROCARBONS AND THEIR USES

BACKGROUND OF THE INVENTION

Silylated hydrocarbons are used for several purposes, including crosslinking polymers, as hydrophobic agents for masonry surfaces and as surface treatments. Specifically, the use of alkoxysilane-containing aliphatic hydrocarbons for making concrete or other masonry surfaces hydrophobic is well known. These silylated hydrocarbon are most usually of the structure $R^1Si(OR^2)_3$ where $R^1=C_1-C_{18}$ straight-chained or branched alkane and $R^2=$an alkyl group of 1 to 4 carbon atoms.

The use of silylated hydrocarbons to crosslink room temperature vulcanizing silicone sealants is well documented as well. The sealants usually contain linear silanol terminated polydimethylsiloxanes, a silylated hydrocarbon of the formula $RSiY_3$, where R is an alkyl radical, and Y is a readily hydrolyzable alkoxy group, and a condensation catalyst. The silylated hydrocarbon readily reacts with the terminal silanol group of the polysiloxane producing an alkoxy-terminated polysiloxane which readily reacts with atmospheric moisture in the presence of condensation catalysts to give a cured silicone rubber.

Specifically, certain bis-silylated hydrocarbons have been known for use in these applications to obtain the additional benefit of having two silane groups. Exemplary bis-silanes include $(CH_3O)_3Si(CH_2)_6Si(OCH_3)_3$ and $(CH_3O)_3Si(CH_2)_2Si(OCH_3)_3$. Additionally, U.S. Pat. No. 5,032,636 to Ono and Yoshioka describes the hydrosilation of 1,9-decadiene with trimethoxysilane in the presence of platinum to produce 1,10- bis(trimethoxysilyl)decane, $(CH_3O)_3Si(CH_2)_{10}Si(OCH_3)_3$. However, these bis-silanes have experienced some problems in actual usage, including toxicity, and are therefore undesirable.

Certain cyclic silylated hydrocarbons have been known in the art as well, but most of these are styrene derived, and many are mono-silylated compounds and/or have the silicon atom bonded directly to the ring or through only one carbon atom, which provides for slow hydrosilation to produce said molecules, and results in silanes which are slow to cure.

SUMMARY

This invention includes silanes comprising (alkyl)alkoxy- and (alky)halosilylalkyl cyclic pentanes and vinyl or allyl -functional (alkyl)alkoxy- and (alkyl)halosilylalkyl cyclic pentanes and their use as crosslinkers, as hydrophobic agents and as siliceous filler treatment. The silylated cyclic hydrocarbons are prepared by the hydrosilation or partial hydrosilation of di- or tri - vinyl or allyl substituted cyclic pentanes with trialkoxysilanes or (alkyl)halosilanes in the presence of a platinum catalyst.

DESCRIPTION OF THE INVENTION

Composition

The silanes described in this invention are di- and trifunctional halosilylalkyl- or alkoxysilylalkyl cyclic hydrocarbons, which may have substituents thereon, including vinyl groups. The cyclic hydrocarbons are cyclopentanes ($C_5$), which may have substituents thereon. Multiple silane functionalities may be attached to the ring. The silane functionalities may have the standard substituents thereon, including alkyl and alkoxy groups and halogens. The silane functionalties are attached to the ring through an alkyl group, of at least $C_2$, which may have substituents thereon. It is important that the alkyl linking group have at least two carbons therein because this allows for the silane to cure relatively quickly and results in a flexible silane.

The specific silanes contemplated herein have the following formula:

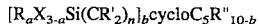

$$[R_aX_{3-a}Si(CR'_2)_n]_b cycloC_5R''_{10-b}$$

where R is an alkyl or aryl group, X is a halogen or an alkoxy radical of 1 to 4 carbon atoms, aryloxy radical, or oxime group, R' is a hydrogen or alkyl group of 1 to 3 carbon atoms, R" is a vinyl, alkyl, allyl, aryl, aryloxy or alkoxy group or hydrogen, a=0 to 2, n=2 to 3 and if at least one R" is an allyl or vinyl group, b=1 to 5, otherwise b=2 to 5. Each X, R, R' or R" may be the same or different from each other. Examples of R are octyl, methyl and phenyl. Examples of X include octyloxy, t-butoxy and more preferably chlorine, methoxy and ethoxy. Examples of R' include methyl and hydrogen, with hydrogen being preferred. Examples of R" include methyl, methoxy, hydrogen and vinyl, with hydrogen and vinyl being preferred. N is preferably 2 to 4, and more preferably 2. "b" is preferably 1 to 3, and more preferably 2 to 3.

Specific examples of the silytalkylcyclic hydrocarbons described above are 1,2-bis[(2-trimethoxysilyl)ethyl]cyclopentane, 1,2,4-tris[(3-tri(methylethylketoximino)silylpropyl cyclopentane and 1,2,4-tris[(2-trimethoxysilyl)ethyl] cyclopentane. Specifically contemplated as substituents on the ring (R") are one or two vinyl groups in conjunction with a commensurate number of trialkoxysilyl groups. Examples of these compositions include 1-vinyl-3-[(2-trimethoxysilyl)ethyl]cyclopentane and 2,4 divinyl-1-[(2-trimethoxysilyl)ethyl]cyclopentane.

Structurally, an example, may be represented figuratively as follows:

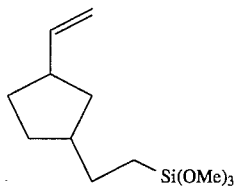

1-vinyl-3-[(2-trimethoxysilyl)ethyl]cyclopentane

Manufacture

The starting materials for making the silylated hydrocarons of the present invention are monomeric polyvinyl or polyallyl cyclopentane and hydrido(alkyl)alkoxysilanes or hydrido(alkyl)halosilanes. A process to prepare monomeric is polyvinyl cyclopentanes is described in U.S. Pat. No. 5,264,606 to Moloy and Dombek, which is incorporated herein by reference. Other references teaching the manufacture of divinylcyclopentanes are German Patent Nos. 4,009,910 and 3,940,196 and U.S. Pat. No. 3,424,811 to Mango. All of these patents describe metathesis processes for the manufacture of divinylcyclopentanes from norbornene and ethylene.

It is important to note that the starting materials for the products herein are not cyclic hydrocarbons with the unsaturated point of attachment for the silanes internal to the ring. Such unsaturations cause manufacturing difficulties because they do not hydrosilate quickly and isomerize during synthesis.

Some exemplary starting olefins for use herein are:

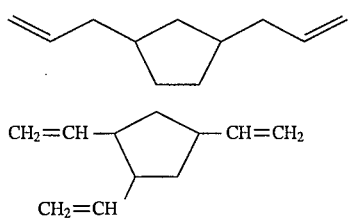

The desired hydrido(alkyl)alkoxysilane or hydrido(alkyl)halosilane are manufactured as is well known in the art as disclosed in Comprehensive Handbook on Hydrosilylation, Marcienic, ed. (1992).

The silane functional hydrocarbons of the present invention are prepared by hydrosilation of the vinyl/allyl substited cyclic hydrocarbon with a hydrido(alkyl)alkoxysilane or hydrido(alkyl)halosilane in the presence of a noble metal catalyst such as platinum, at elevated temperature (50° C. to 120° C.). Similar hydrosilation reactions are well known in the art. See for example, the *Comprehensive Handbook on Hydrosilylation*, supra.

Use

The silylated-hydrocarbons of the present invention are useful as crosslinkers in silicone room temperature vulcanizable (RTV) caulks to increase the crosslink density of the sealant and thus increase the modulus or toughness of these materials as compared to the same compositions without these additives. The silylated hydrocarbons may also be used as hydrophobic agents for masonry surfaces. Another potential use of compounds of the present invention is as a reactive viscosity reducer in coatings involving silylated materials. Another use of compounds of the present invention is as a reactive viscosity reducer in coatings involving silylated materials. Application of the silylated hydrocarbons of the present invention to siliceous and aluminate fillers and mixing these treated fillers into polyethylene, EPM, or silicone rubber provide extra reinforcement to the compound, thereby increasing its toughness. The silanes for such use, however, must contain an unreacted unsaturated group external to the ring after the completion of hydrosilation.

EXAMPLES The following examples are presented to illustrate the present invention.

Example 1

Preparation of 1,3,4-tris[(2-trimethoxysilyl)ethyl]cyclopentane

To a one liter, three-necked flask, equipped with a heating mantle, mechanical stirrer, addition funnel, thermometer and distillation head and protected with nitrogen, was added 148.2 grams (1.0 mole) of 1,3,4-trivinylcyclopentane. With stirring, the contents of the flask were heated to 95° C. and 15 ppm of platinum, as chloroplatinic acid (based on the total weight of reactants) in glyme (1,2 dimethoxyethane)/isopropanol and 1.29 grams (0.25 wt. %) acetic acid were added. Immediately, from the addition funnel, were added dropwise 370.3 grams (3.03 moles) of trimethoxysilane, adjusting the rate of addition to maintain the contents of the flask at 95–110° C. from the heat of reaction. After the addition was complete, heat was applied and maintained at 95° C. for 1 hour to assure reaction completion. The acetic acid and excess trimethoxysilane were distilled from the reaction mixture to 110° C. and 1 Torr, yielding 470 grams (91.3% yield) of product. A gas chromatographic analysis of the flask contents indicated >86% contained product and a $^1$H NMR analysis confirmed this product to be 1,3,4-tris[2-(trimethoxysilyl)ethyl]cyclopentane.

Example 2

Preparation of 1,3-Bis[2-(trimethoxysilyl)ethyl]cyclopentane

To a three liter, three-necked flask, equipped with a heating mantle, mechanical stirrer, addition funnel, thermometer and distillation head and protected with nitrogen, was added 458.3 grams (3.75 moles) of 1,3-divinylcyclopentane and 2.86 grams (0.25 wt. %) of acetic acid. The contents of the flask were heated with stirring to 95° C. whereupon 10 ppm platinum., as chloroplatinic acid dissolved in glyme/isopropanol and 2.86 grams of acetic acid were added to the flask. From the addition funnel was added dropwise 955.5 grams (7.8 moles) of trimethoxysilane. Initially, the reaction was exothermic and the temperature of the flask contents rose to 105° C. The temperature was maintained at 95–110° C. by external cooling and addition rate of the trimethoxysilane. An additional 10 ppm platinum was added near the end of the trimethoxysilane addition to ensure reaction completion. The reaction temperature was maintained at 95° C. for an additional 2 hours by an external heater, distilled of acetic acid and excess trimethoxysilane, cooled, treated with decolorizing carbon, and filtered to yield 1210 grams (88% yield) of product. Gas chromatography indicated >92% product purity. The structure was confirmed by NMR analysis to be 1,3-bis[2-(trimethoxysilyl)ethyl]cyclopentane.

Example 3

Preparation of 1,3-Bis[2-(dichloromethylsilyl)ethyl]cyclopentane

To a one liter three-necked reaction vessel equipped with a magnetic stirrer, a heating mantle, a thermometer, addition funnel, a distillation head, and protected by a dry nitrogen bypass was charged 122 grams (1.0 mole) of 1,3-divinylcyclopentane. The flask contents were heated with stirring to 75° C., 25 ppm of platinum, as chloroplatinic acid (based on total reactants) as a solution in glyme/isopropanol, and 253.0 grams (2.2 moles) of dichloromethylsilane was added from the addition funnel. Immediately upon addition of the dichloromethylsilane an exothermic reaction ensued, necessitating removal of the heating mantle adjusting the rate of addition of dichloromethylsilane to maintain the contents of the flask at 80°–90° C. After the addition of all of the hydridosilane, the reaction mixture was heated to 80°–90° C. for about 1 hour to ensure complete reaction. The flask contents were cooled to room temperature, the excess dichloromethylsilane was removed by vacuum distillation, to yield 312.2 grams (88.6% yield). A gas chromatographic analysis of the reaction mixture indicated 75% product purity. The composition of the reaction mixture was confirmed by $^{13}$C NMR analysis to contain 1,3 bis[2-(dichloromethylsilyl)ethyl]cyclopentane with a minor amount of 1-[(2-dichloromethylsilyl)ethyl]-3-vinylcyclopentane.

Example 4

Preparation of 1,3-Bis[(2-dimethoxymethylsilyl)ethyl]cyclopentane

To the reaction product of Example 3 was added subnatently with stirring at 50° C. under a vacuum of 50 Torr, 279 grams (8.7 moles) of anhydrous methanol. The by-product HCl was continuously removed. After the methanol addition, an analysis of the flask contents indicated 0.25% chloride. A gas chromatographic analysis of the product showed >72% purity. NMR (both $^1$H and $^{13}$C) analyses of the product showed that it consisted mainly of 1,3-bis[(2-dimethoxymethylsilyl)ethyl]cyclopentane with minor amounts of 1-[(2-dimethoxymethylsilyl)ethyl]-3-vinylcyclopentane.

Example 5

Preparation of 1,3-Bis[(2-trichloro)ethyl]cyclopentane

To a one liter, three-necked flask, equipped with a heating mantle, mechanical stirrer, addition funnel, thermometer and distillation head and protected with a nitrogen by-pass, was added 122.2 grams (1.0 mole) of 1,3-divinylcyclopentane. With stirring, the contents of the flask were heated to 80° C. and 25 ppm of platinum, as chloroplatinic acid (based on the total weight of reactants) dissolved in glyme/isopropanol was added. From the addition funnel 298.0 grams (2.2 moles) of trichlorosilane were added dropwise. After the first few grams of trichlorosilane were added, an exothermic reaction ensued. The heating mantle was removed from the reaction vessel and the rate of addition was adjusted to maintain the reaction temperature at 75°–88° C. After the addition was complete, the flask contents were heated at 80° C. for 3 hours to ensure reaction completion. After cooling, the excess trichlorosilane was distilled from the reaction mixture under vacuum to yield 362.0 grams (92% yield). A gas chromatographic analysis the product purity to be >92%. Both $^1$H and $^{13}$C NMR analyses indicated the composition to be 1,3-bis[(2-trichlorosilyl)ethyl]cyclopentane.

Example 6

Preparation of 1-Vinyl-3 [(2-trimethoxysilyl)ethyl]cyclopentane

To a 1 liter three-necked flask, equipped as in Example 4 was added 122 grams (1.0 mole) of 1,3-[divinyl]cyclopentane. The flask contents were heated with stirring to 85° C, and 10 ppm platinum (as chloroplatinic acid dissolved in glyme/isopropanol)was added. From the addition funnel was slowly added 122 grams (1.0 mole) of trimethoxysilane. An immediate exotherm was noted, and the heating mantle was removed from the flask and the temperature was maintained at 85°–90° C. by the rate of addition of trimethoxysilane. After the trimethoxysilane was added, a gas chromatographic analysis of a sample of the reaction mixture indicated 15% divinylcyclopentane, 50% 3-vinyl-1-[(2-trimethoxysilyl)ethyl]cyclopentane, and 34% 1,3-bis [(trimethoxysilyl)ethyl]cyclopentane. The flask was set up for vacuum distillation and three cuts were taken. The first cut, 34 grams, was shown to be unreacted 1,3-divinylcyclopentane by NMR analysis. The second cut (bp=75°–77° C. at 0.4 Torr), was 97.6 grams (40% yield) and was found to be 1-vinyl-3-[(2-trimethoxysilyl)ethyl]cyclopentane by mass spectroscopy, $^1$H and $^{13}$C NMR spectroscopy. The third cut (bp=131°–133° C. at 0.4 Torr) was 69 grams and was found to be identical to the product of Example 2 by NMR analysis.

Example 8

Hydrophobicity Testing on Concrete

Each silane listed in Table 1 below was dissolved in Mineral Spirits to a concentration of 40%, applied to 2 inch concrete cubes at a rate of 125 square feet per gallon with a small bristle brush, and allowed to cure on a wire rack for 2 days. The coated cubes were then weighed and immersed in a water bath so that the top of the concrete cube was more than one inch below the water surface. The cubes were kept submerged for eight days. After completion of the test, the cubes were allowed to dry at ambient conditions, weighed, the weight gain noted, then they were broken in half. The inner surface of each cube was sprayed with water and the depth of penetration of each silane-functional cyclopentane was determined as a visible dry area of the concrete below the surface. The results are summarized in Table 1.

TABLE 1

| Sample | % Wt. Gain after 8 Days | Hydrophobic Layer (depth in inches) |
|---|---|---|
| Control (no silane) | 6.0 | 0.0 |
| Silane of Example 1 | 1.87 | 0.1 |
| Silane of Example 2 | 1.29 | 0.15 |
| Silane of Example 4 | 3.14 | 0.15 |

The results of Table 1 clearly indicate that the silylated hydrocarbons of the present invention impart a hydrophobic character to concrete, as demonstrated by the small percentage of weight gain of the concrete cubes after standing in water for 8 days (compared to a control with no silane treatment).

Example 9

Crosslinking Capability with a Silanol-terminated Polydimethylsiloxane

To 60 parts of silanol-terminated polydimethylsiloxane (50,000 centistokes; Hüls America PS347.5), 4 parts of the desired crosslinker, and 0.1 part of dibutyltin dilaurate condensation catalyst were mixed for several minutes by hand prior to casting a film (6 inches×4 inches×0.125 inches). The film was allowed to cure under ambient conditions (approximately 23° C., 40–60% relative humidity) and finger touch tack free time was monitored. Physical properties were obtained on completely cured samples (7 days at 23° C., 50% relative humidity) according to the following ASTM test specifications: ASTM C-661 (Shore A hardness), ASTM C-D-412 (% elongation, tensile strength, and modulus) and ASTM D-624 (tear).

TABLE 2

|  | A | B | C |
|---|---|---|---|
| Formulation |  |  |  |
| Silanol fluid (50,000 cstk) | 60 phr | 60 phr | 60 phr |
| Methyltrimethoxysilane | 4 phr | 0 | 0 |
| Product of Example 1 | 0 | 4 phr | 0 |
| Product of Example 2 | 0 | 0 | 4 phr |
| Dibutyltin dilaurate | 0.1 phr | 0.1 phr | 0.1 phr |
| Properties |  |  |  |
| Hardness (Shore A) | 14 | 35 | 33 |
| Tack free time (min) | 45 | 60 | 40 |
| Elongation (%) | 145 | 151 | 114 |
| Tensile Strength (psi) | 22.2 | 64.5 | 55.9 |
| Young's Modulus (psi) | 25.9 | 68.8 | 73.9 |
| Tear (lbs/in) | 3.44 | 13.8 | 6.9 |

As can be seen from Table 2, a significant increase in the tensile strength, Young's Modulus, and tear was observed for Formulations B and C, containing the products of Examples 1 and 2, respectively, compared to a standard crosslinker used as a control, methyltrimethoxysilane (Formulation A).

I claim:

1. A silane composition comprising:

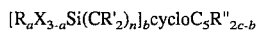

where R is an alkyl or aryl group, X is a halogen or an alkoxy radical of 1 to 4 carbon atoms, aryloxy radical or oxime group, R' is a hydrogen or alkyl group of 1 to 3 carbon atoms, R" is a vinyl, alkyl, allyl, aryl, aryloxy or alkoxy group or hydrogen, a=0 to 2, n=2 to 3 and if at least one R" is a vinyl or allyl group, b=1 to 5, otherwise b=2 to 5.

2. A silane according to claim 1 wherein every R' is hydrogen and n=2.

3. A silane according to claim 1 wherein every R" is hydrogen.

4. A silane according to claim 1 wherein one R" is a vinyl group and b=2.

5. A composition according to claim 1 additionally comprising a silicone room temperature vulcanizable sealant.

6. A silane composition according to claim 1 wherein n=2 to 3.

7. A silane composition according to claim 1 wherein b=1 to 3.

8. A silane composition according to claim 1 wherein where R is selected from the group consisting of: octyl, methyl and phenyl.

9. A silane composition according to claim 1 wherein X is selected from the group consisting of: octyloxy, t-butoxy, chlorine, methoxy and ethoxy.

10. A silane composition according to claim 1 wherein R' is selected from the group consisting of: methyl and hydrogen.

11. A silane composition according to claim 1 wherein R" is selected from the group consisting of methyl, methoxy, hydrogen and vinyl.

12. A silane composition according to clam 1 wherein the silane composition is selected from the group consisting of: 1,2-bis[(2-trimethoxysilyl)ethyl]cyclopentane, 1,2,4-tris[(3-tri(methylethylketoximino)silylpropyl cyclopentane, 1,2,4-tris[(2-trimethoxysilyl)ethyl]cyclopentane, 1-vinyl-3-[(2-trimethoxysilyl)ethyl]cyclopentane and 2,4 divinyl-1-[(2-trimethoxysilyl)ethyl]cyclopentane.

13. A composition according to claim 1 wherein the silane has an unreacted unsaturated group external to the ring and additionally comprising (i) siliceous or aluminate fillers and (ii) polyethylene, EPM, or silicone rubber.

* * * * *